(12) United States Patent
Stenton et al.

(10) Patent No.: US 6,943,897 B1
(45) Date of Patent: Sep. 13, 2005

(54) METHOD OF FABRICATING AND INSPECTING A TRANSPARENT OPTICAL ELEMENT HAVING A PARABOLIC OPTICAL-QUALITY LATERAL SURFACE

(75) Inventors: Conrad Stenton, Midland (CA); Richrd Henzelt, Penetang (CA)

(73) Assignee: Raytheon Company, Waltham, MA (US)

( * ) Notice: Subject to any disclaimer, the term of this patent is extended or adjusted under 35 U.S.C. 154(b) by 279 days.

(21) Appl. No.: 10/401,306

(22) Filed: Mar. 26, 2003

(51) Int. Cl.[7] ............................................. G01B 9/02
(52) U.S. Cl. ...................................................... 356/515
(58) Field of Search ................................ 356/512, 513, 356/514, 515

(56) References Cited

U.S. PATENT DOCUMENTS

| | | | | |
|---|---|---|---|---|
| 5,864,402 A | * | 1/1999 | Stenton | 356/515 |
| 5,867,272 A | * | 2/1999 | Stenton | 356/508 |
| 6,480,284 B1 | * | 11/2002 | Stenton | 356/458 |

* cited by examiner

Primary Examiner—Gregory J. Toatley, Jr.
Assistant Examiner—Michael A. Lyons
(74) Attorney, Agent, or Firm—William C. Schubert; Karl A. Vick

(57) ABSTRACT

An optical element is fabricated and inspected by forming a spherical-segment surface in a light-transparent blank at a first end thereof with a spherical-segment center on an element axis of the light-transparent blank. A trial parabolic surface is formed in a lateral surface of the light-transparent blank with a trial-surface parabolic focus coincident with the spherical segment center. The trial parabolic surface is inspected by directing a source light beam from a light source through the light-transparent blank parallel to the element axis and against the trial parabolic surface, whereupon a reflected light beam reflects back substantially parallel to the source light beam but oppositely directed to the source light beam. The reflected light beam is optically interfered with the source light beam to produce an interference pattern. The shape of the trial parabolic surface is corrected responsive to observations of the interference pattern to produce a final parabolic surface having a final parabolic focus coincident with the spherical-segment center.

20 Claims, 3 Drawing Sheets

METHOD OF FABRICATING AND INSPECTING A TRANSPARENT OPTICAL ELEMENT HAVING A PARABOLIC OPTICAL-QUALITY LATERAL SURFACE

This invention relates to the fabrication of a transparent optical element with a precisely shaped parabolic optical-quality lateral surface thereon and, more particularly, to such an optical element having a spherical surface at an end thereof.

BACKGROUND OF THE INVENTION

For some applications, it is desirable to produce an optical-quality, parabolic optical surface on a lateral surface of a light-transmissive solid body. A light beam directed through the light-transmissive solid body parallel to the parabolic axis and toward the parabolic surface is reflected from the parabolic surface to pass through the parabolic focus. Similarly, a light beam originating at the parabolic focus reflects from the parabolic surface and travels parallel to the parabolic axis. For example, a glass (for visible light) or silicon (for infrared light) solid-body optical element having its lateral surface formed to the parabolic shape may be required for various types of optical applications.

The fabrication of a parabolic lateral surface on a light-transparent body is typically performed by a combination of grinding and polishing the lateral surface of the light-transparent body. The shape of the lateral surface must be carefully measured as the grinding and polishing proceeds, to ensure that the final lateral surface will have the required precisely parabolic shape. Thus, during the grinding-and-polishing operation the shape of the surface may be periodically checked by mechanical inspection techniques to be certain that it is converging on the desired parabolic shape. The grinding-and-polishing procedure is altered and fine-tuned as a result of the measurements, to achieve the desired final parabolic shape.

While this approach is operable to some extent, it has drawbacks. The mechanical inspection procedure is cumbersome and difficult to perform without removing the light-transparent body from the grinding-and-polishing apparatus. The degree of precision required may also be greater than can readily be determined by mechanical measurements. As the lateral surface approaches its final shape, achieving a precisely curved surface is therefore difficult.

There is a need for an improved approach to the fabrication of a parabolic optical lateral surface on a light-transparent body. The present invention fulfills this need, and further provides related advantages.

SUMMARY OF THE INVENTION

The present invention provides an approach for fabricating and inspecting a light-transmitting optical element with a lateral parabolic surface. The inspection may be performed at intermediate stages of the fabrication with the optical element in its fabrication apparatus, so that the fabrication procedure may be adjusted to ensure that the fabrication leads to an optical-quality parabolic surface. The inspection procedure is accomplished optically in a high-precision manner, ensuring that the final parabolic surface parabolic surface is of the required optical quality.

In accordance with the invention, a method for fabricating and inspecting an optical element comprises the steps of furnishing a light-transparent blank having an element axis, and thereafter forming a spherical-segment surface in the light-transparent blank at a first end thereof, with a spherical-segment center on the element axis. The method further includes forming a trial parabolic surface in a lateral surface of the light-transparent blank spaced apart from the element axis. The trial parabolic surface has a trial-surface parabolic focus substantially coincident with the spherical-segment center. The trial parabolic surface is inspected by directing a source light beam from a light source through the light-transparent blank parallel to the element axis and against the trial parabolic surface, whereupon a reflected light beam reflects back substantially parallel to the source light beam but oppositely directed to the source light beam. The reflected light beam is optically interfered with the source light beam to produce an interference pattern. The interference pattern indicates the degree of approach of the trial parabolic surface to a mathematically correct parabolic surface. Preferably, after the step of inspecting, the shape of the trial parabolic surface is corrected responsive to the interference pattern to produce a final parabolic surface having a final parabolic focus coincident with the spherical-segment center. The spherical-segment surface may be a spherical-segment cavity or a spherical-segment protrusion.

In the inspection procedure, the source light beam passes through the transparent optical blank and optical element, and reflects from the trial parabolic surface substantially toward the trial-surface parabolic focus. The light beam reflects from the spherical-segment surface, and back toward the trial parabolic surface. The reflected light beam reflects again from the trial parabolic surface and back toward the light source. In the early stages of fabrication when the trial parabolic surface deviates considerably from a true mathematical parabolic shape, the intensity of the reflected light beam may be small, and there is not a strong interference pattern with the source light beam. The shape of the trial parabolic surface is corrected, so that it becomes closer to a mathematical parabola, and re-inspected. After a sufficient number of iterations, when the trial parabolic surface approaches a true mathematical parabolic shape, the interference pattern forms strongly and may be used to correct and adjust the shape of the trial parabolic surface until it eventually becomes a true mathematic parabola to within the limits of the degree of perfection required for the particular application. In this processing, the coarser shaping of the trial parabolic surface is preferably accomplished by grinding, and the finer shaping by polishing.

One of the problems encountered in this technique is the possibility of an insufficiently strong reflection from the spherical-segment surface. A reflective coating may be applied to the spherical-segment surface to improve its reflectivity. The intensity of the reflected light beam may instead be increased by positioning a spherical retroreflector external to the first end of the light-transparent blank with a spherical-retroreflector center coincident with the spherical-segment center, so that the light beam passes out of the light-transparent blank through the spherical-segment surface, reflects from the spherical retroreflector, and re-enters the light-transparent blank through the spherical surface.

The present approach uses the interferometric optical inspection procedure to ensure that the shape of the lateral surface approaches a parabola, and that it is of optical quality. Because the inspection procedure is based on highly precise light measurements and the continued re-shaping of the lateral surface is performed responsive to this optical inspection procedure, the final optical element necessarily has the required optical-quality lateral parabolic surface. Additionally, as will be discussed subsequently, the optical inspection apparatus may be established on the same support structure and fixturing as required for the forming and shaping of the lateral surface, so that there is only a single set-up required. Set-up is less costly than in prior approaches, and there is no loss of quality of the parabolic lateral surface as a result of repeated set-up errors.

The spherical-segment surface may be present because it is a further functional part of the optical element, and in a presently preferred application that is the case. The spherical-segment surface may instead be provided solely to facilitate the inspection procedure, and then left in place in, or removed from, the final optical element at the completion of its fabrication.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
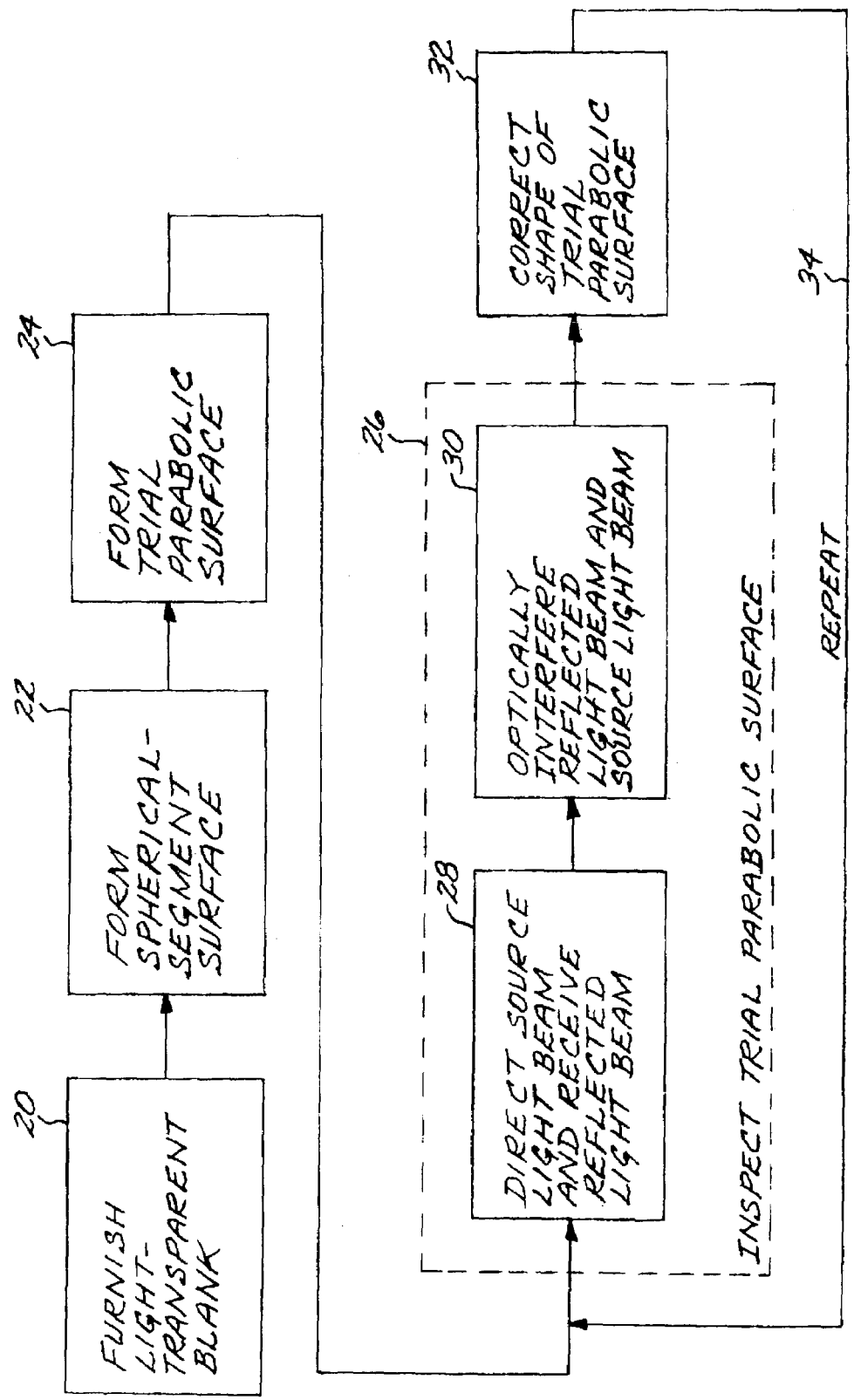
FIG. 1 is a block flow diagram of an approach for practicing the invention.
Figure 2:
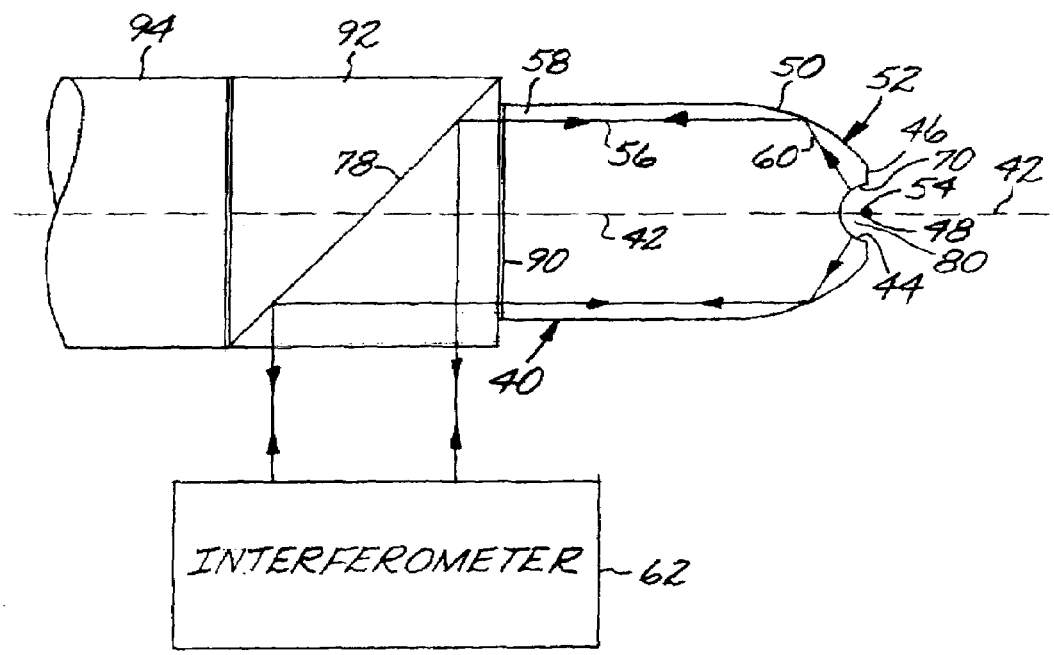
FIG. 2 is a schematic sectional view of a fabrication-and-inspection apparatus with the light-transparent blank in place.
Figure 3:
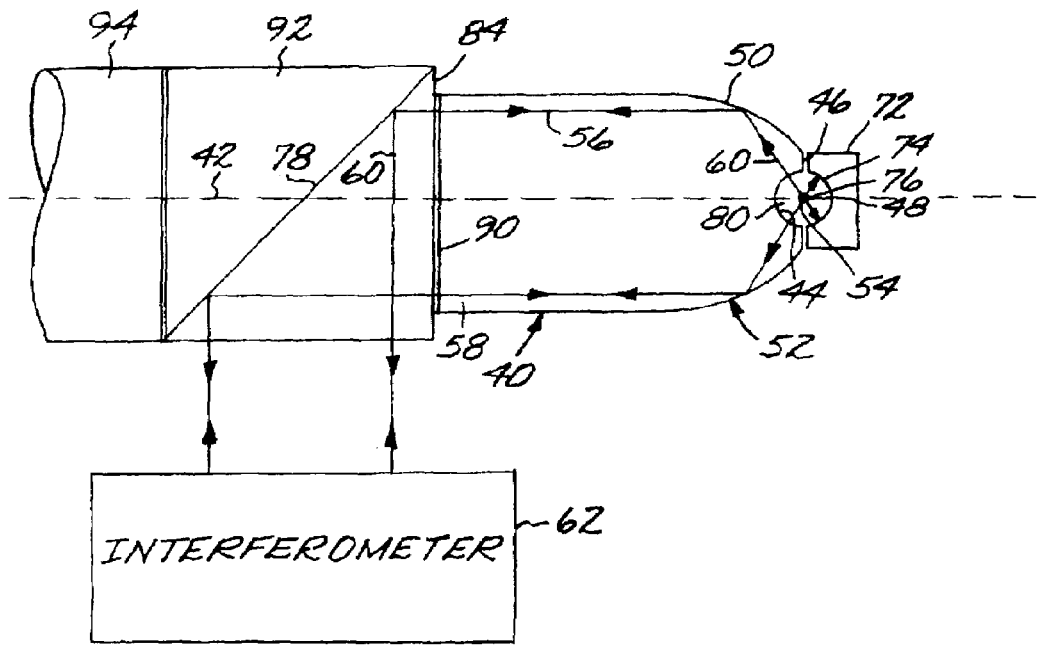
FIG. 3 is a schematic sectional view like that of FIG. 2, but with a spherical retroreflector added.
Figure 4:
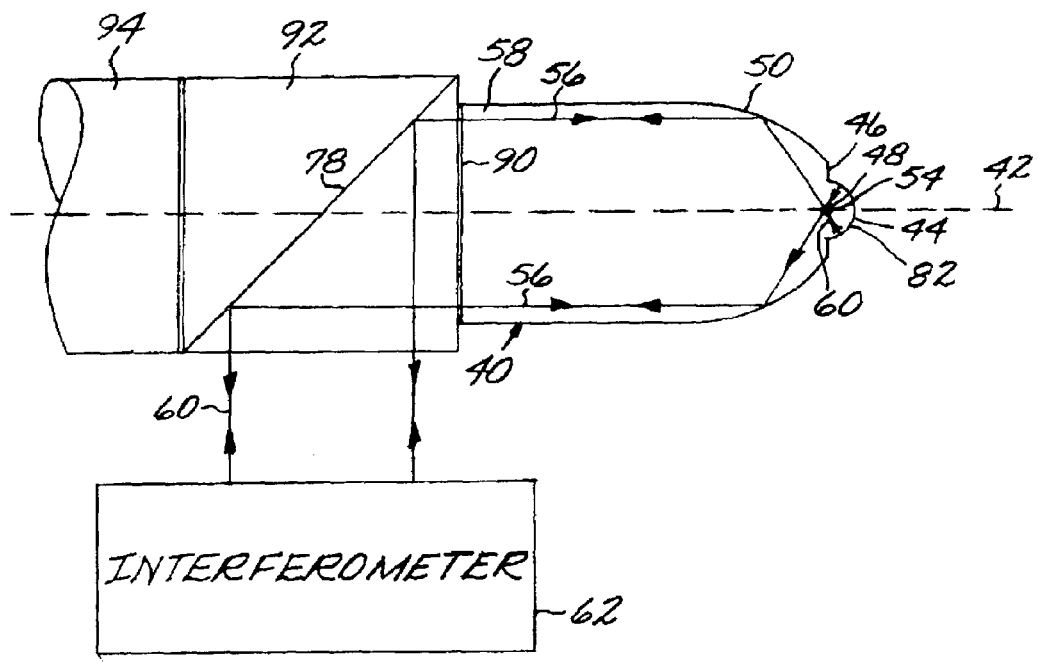
FIG. 4 is a schematic sectional view like that of FIG. 2, but with a spherical segment that is a protrusion.
Figure 5:
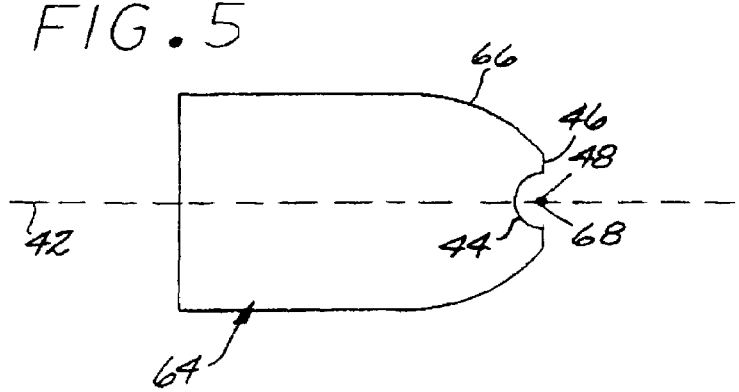
FIG. 5 is a schematic sectional view of a completed optical element with a final parabolic surface.

FIG. 1 depicts a method for fabricating and inspecting an optical element, FIGS. 2–4 illustrate the structures associated with the method, and FIG. 5 illustrates the completed optical element. In the figures, some surfaces may not have the ideal shapes (e.g., plane, spherical, parabolic) or geometrical orientation as described herein due to the limitations of drawing such idealized shapes, and in such cases the text description is to be taken as correct.

A solid (in the sense of solid as distinct from liquid or gas) light-transparent blank 40 having an element axis 42 is furnished, step 20. The light-transparent blank 40 serves as a starting piece or workpiece that is fabricated to form the optical element. The light-transparent blank 40 is transparent to light in the wavelengths of interest. For example, for an optical element to be used in the visible range, the light-transparent blank 40 may be glass; for an optical element to be used in the infrared range, the light-transparent blank 40 may be silicon. The light-transparent blank 40 may be of any operable shape and size, but preferably it is of an external shape generally similar to that of the final optical element, but slightly larger in size to permit material to be removed in the shaping of the surfaces but not so large as to require excessive removal of material. The element axis 42 provides a reference line. In some cases, the final optical element is rotationally or otherwise symmetric about the element axis 42, although that need not be the case. The light-transparent optical blank may be described as having a first end 46, adjacent to which the parabolic surface is to be formed, and an oppositely disposed second end 58.

For the preferred approach, the light-transparent blank 40 has a planar surface 90 lying perpendicular to the element axis 42, at the second end 58 of the light-transparent blank 40. The light-transparent blank 40 may be furnished with such a planar surface 90, or it may be fabricated into the light-transparent blank and tested. The planar surface 90 may optionally be coated with an anti-reflective coating, for reasons to be discussed subsequently.

For the preferred approach, the planar surface 90 is affixed to an uncoated face of a cube-shaped, transparent prism block 92 having an internal fold mirror 78 on an edge-to-edge diagonal thereof, using an index-of-refraction-matching optical cement that may be later dissolved to separate the final optical element from the prism block 92. This prism block 92 and its fold mirror 78 allow light signals to be introduced into, and received from, the light-transparent blank from the side. For the preferred case where the final optical element is rotationally symmetric about the element axis 42, the opposite side of the prism block 92 is affixed, preferably with a dissolvable adhesive, to a rotatable spindle 94 of a shaping machine which is used to shape the lateral surface, as by grinding and polishing. The light-transparent blank 40 is affixed to the spindle 94 so that the element axis 42 coincides with the axis of rotation of the spindle 94. The light-transparent blank 40 is thereby affixed to the shaping machine, and remains affixed to the shaping machine when the subsequent steps of shaping (steps 24 and 32) and inspection (step 26) are performed.

A spherical-segment surface 44 is thereafter formed, step 22, in the light-transparent blank 40 at the first end 46 thereof. The spherical-segment surface 44 is a portion (segment) of the surface of a sphere, such as, but not necessarily, a hemisphere. The spherical-segment surface 44 has a spherical-segment center 48, which is the center of the sphere defining the spherical-segment surface 44, lying on the element axis 42. The spherical-segment surface 44 is formed by any operable approach, with a combination of grinding and polishing being preferred. Techniques for forming such spherical-segment surfaces 44 are known in the art.

A trial parabolic surface 50 is formed in an external, outwardly facing lateral surface 52 of the solid light-transparent blank 40, step 24. The trial parabolic surface 50 is spaced apart from the element axis 42, with the solid light-transparent material between the trial parabolic surface 50 and the elemental axis 42. (That is, the parabolic surface is not on an inwardly facing surface of a mirror that faces toward its axis of symmetry.) The trial parabolic surface 50 has a trial-surface parabolic focus 54 that is ideally substantially coincident with the spherical-segment center 48. However, at this early stage of fabrication the trial-surface parabolic focus 54 and the spherical-segment center 48 may not coincide perfectly. In the preferred application, the trial parabolic surface 50 is approximately rotationally symmetrical about the element axis 42.

The parabolic surface 50 is a "trial" parabolic surface because it is the initial best effort at defining the final parabolic surface. That is, according to the present approach the trial parabolic surface 50 is first formed and is thereafter inspected to determine the extent of its departure from a mathematically perfect parabola with the focus 54. This inspection information is used to refine the trial parabolic surface 50 until it approaches the mathematically perfect parabola to the extent sought by for a particular application.

The trial parabolic surface 50 is thereafter inspected, step 26. As shown in the schematic ray path drawing of FIG. 2, the inspection 26 is performed by directing a source light beam 56 from a light source that is preferably within an interferometer 62, through the planar surface 90 and into the light-transparent blank 40, and through the light-transparent blank 40 parallel to the element axis 42 and against the trial parabolic surface 50, step 28. (A small portion of the source light beam reflects from the planar surface 90, to serve as the reference for the subsequent interference.) The source light beam 56 reflects from the trial parabolic surface 50 toward the trial-surface parabolic focus 54 by total internal reflection. Because the trial-surface parabolic focus 54 is also the spherical-segment center 48, the source light beam 56 is perpendicularly incident upon the spherical-segment surface 44 and, ideally for the present purposes, reflects from it as a reflected light beam 60 because the spherical-segment surface 44 is an interface between the material of the light-transparent blank 40 and the air having a lower index of refraction. The reflected light beam 60 beam reflects back from the spherical-segment surface 44 substantially parallel to and coincident with the source light beam 56 but oppositely directed to the source light beam 56, reflects from the trial parabolic surface 50, and passes out of the second end 58 of the light-transparent blank 40 along substantially the inverse path of the source light beam 56. The prism blank 92 and its fold mirror 78 direct the light beams 56 and 60 from and to the interferometer 62.

The reflected light beam 60 passes out of the light-transparent blank 40 and is optically interfered, step 30 of FIG. 1, with the reflection of the source light beam 56 (that is reflected from the planar surface 90) to produce an interference pattern. It is desirable that the reflected light beam 60 be of approximately the same intensity as the reflection of the source light beam 56 from the planar surface 90, so as to achieve the optimal interference pattern. To this end, the optical-segment surface 44 may be coated with a reflective coating to increase the intensity of the reflected light beam 60, and/or the planar surface 90 may be coated with an anti-reflective coating to reduce the intensity of the reflection of the source light beam 56 from the planar surface 90. The reflected light beam 60 and the reflection of the source light beam 56 that are optically interfered each have about the same light intensity, about 4 percent that of the source light beam 56 in a typical case.

The optical interference between the light beams 56 and 60 is preferably accomplished in a conventional interferometer 62, schematically illustrated in FIG. 2. In the preferred approach, the planar surface 90 of the light-transparent blank is affixed with optical cement to the prism block 92 having the 45 degree fold mirror 78 therein, which reflects the light beams 56 and 60 from and to the laterally displaced interferometer 62 located off of the element axis 42. The interferometer 62 may be positioned laterally well away from the light-transparent blank 40 by using the fold mirror 78 to reflect the source light beam 56 and the reflected light beam 60 at an angle to the element axis 42. This approach is particularly advantageous when the light-transparent blank 40 is mounted to the spindle 94 of the grinding/polishing machine as described above, and the relatively delicate interferometer 62 is to be positioned well away from the machine so that it is not damaged during the iterative grinding and polishing steps. Thus, the light-transparent blank 40 is set up initially in the grinding/polishing machine and the interferometer 62 is initially positioned. This arrangement is maintained during the entire fabrication and inspection procedure, reducing errors that could otherwise arise from misalignments in the event that repeated setups and positions are required.

The resulting interference pattern is typically associated with an imperfect parabolic surface, indicating that the trial parabolic surface 50 deviates from the mathematically ideal parabolic surface. One objective of the present approach is to progressively shape and improve the trial parabolic surface 50 so that it is more nearly of the mathematically ideal form. To do so, a shape of the trial parabolic surface 50 is shaped and corrected responsive to the interference pattern to produce a final optical element 64 having its final precisely parabolic surface 66 whose final precisely parabolic focus 68 is coincident with the spherical-segment center 48 along the element axis 42, step 32, as shown in FIG. 7.

The correction is performed by physically altering the shape of the trial parabolic surface 50 in small increments. For most materials of construction of the light-transparent blank 40, the shape alteration is accomplished by polishing the trial parabolic surface 50 to remove imperfections and shape deviations that cause the trial parabolic surface 50 to deviate from the mathematical ideal parabolic surface. In the preferred approach, this shaping is performed as the spindle 94 rotates to rotate the light-transparent blank 40 about the element axis 42. After the shaping and shape correction 32, the inspection 26 is ordinarily repeated, step 34 of FIG. 1. The reshaping and shape correction 32 are then also repeated as needed. Several iterations of steps 26 and 32 may be required. Eventually, the shape of the trial parabolic surface 50 approaches the mathematically ideal parabolic surface sufficiently closely that it is deemed the final parabolic surface 66. The degree of perfection required may vary between different types of final optical elements 64. An important benefit of the present approach is that the inspection used in the shape optimization of the final parabolic surface 66 is performed using an optical technique rather than a mechanical technique. The result is that the character of the final parabolic surface 66 is optimized from an optical standpoint, which is its ultimate utilization, rather than a mechanical standpoint.

At the completion of the fabrication when the parabolic surface has reached the desired degree of perfection, the final optical element 64 is typically separated from the structure that is present to aid in the fabrication and inspection. In the presently preferred approach, the optical cement between the prism block 92 and the planar surface 90 is dissolved, freeing the final optical element 64.

Although ideally the source light beam 56 reflects from the spherical-segment surface 44 sufficiently to produce the optical interference of step 30, in some cases an insufficient fraction of the source light beam 56 is reflected to produce a suitable interference pattern. Any operable and suitable technique may be used to increase the extent of reflection. In one technique illustrated in FIG. 2, a reflective coating 70 is optionally applied to the spherical-segment surface 44 for the purposes of the fabrication and inspection procedure and is later removed when the final optical element is placed into service. The reflective coating 70 may be, for example, a thin silver or aluminum coating deposited by vapor deposition onto the spherical-segment surface 44. In another technique illustrated in FIG. 3, a spherical retroreflector 72 having a highly reflective retroreflector spherical surface 74 in facing relation to the spherical-segment center 48 is positioned external to the first end 46 of the light-transparent blank 40. A spherical-retroreflector center 76 is positioned coincident with the spherical-segment center 48 and thence with the trial-surface parabolic focus 54. The source light beam 56 passes through the spherical-segment surface 44 (which is not coated in this case with the reflective coating 70), and thence leaves the light-transparent blank 40, passes through the center 48, 76, and reflects from the retroreflector spherical surface 74 as the reflected light beam 60. The reflected light beam 60 enters the light-transparent blank 40 through the spherical-segment surface 44, and is reflected to the interferometer 62 to optically interfere with the source light beam 56.

In the embodiments of FIGS. 2–3, the spherical-segment surface 44 is illustrated as the surface of a spherical-segment cavity 80 that is recessed inwardly in the first end 46 of the light-transparent blank 40. Alternatively, the spherical-segment surface 44 may be the surface of a spherical-segment protrusion 82 that extends outwardly from the first end 46 as illustrated in FIG. 4. The latter configuration is particularly useful if the spherical-segment surface 44 is present only for the purposes of inspection, and later is to be removed by cutting off the protrusion.

Other than the variations discussed herein, the embodiments of FIGS. 2–4 all function similarly, and the prior description is applicable to all of these embodiments. The features of the various embodiments may be used interchangeably in any operable combination.

The presently preferred embodiment provides a simultaneous measure of the planarity of the planar surface 90, the sphericity of the spherical-segment surface 44, and the degree to which the lateral surface 52 approaches a parabolic shape. The planarity of the planar surface 90 and the sphericity of the spherical-segment surface 44 may instead be checked and verified separately as they are fabricated into the light-transparent blank 40.

In the present approach, the source light beam 56 is introduced into the light-transparent blank 40 through the planar surface 90 at the second end 58 remote from the first end 46 at which the focus of the parabolic surface is located. Initial evaluations showed that the source light beam cannot be introduced into the light-transparent blank 40 through the first end 46, inasmuch as the subtended angle between the opposite sides of the lateral surface 52 is too great. Also, this approach would produce a measure of the sphericity of the spherical-segment surface 44, rather than provide a measure of the parabolic shape of the lateral surface.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method for fabricating and inspecting an optical element, comprising the steps of
    furnishing a light-transparent blank having an element axis; thereafter
    forming a spherical-segment surface in the light-transparent blank at a first end thereof, wherein the spherical-segment surface has a spherical-segment center on the element axis;
    forming a trial parabolic surface in a lateral surface of the light-transparent blank spaced apart from the element axis, wherein the trial parabolic surface has a trial-surface parabolic focus substantially coincident with the spherical-segment center; and thereafter
    inspecting the trial parabolic surface by
        directing a source light beam from a light source through the light-transparent blank parallel to the element axis and against the trial parabolic surface, whereupon a reflected light beam reflects back from the spherical-segment surface substantially parallel to the source light beam but oppositely directed to the source light beam, and
        optically interfering the reflected light beam with the source light beam to produce an interference pattern.

2. The method of claim 1, wherein the step of furnishing includes the step of
    affixing the light-transparent blank to a shaping machine, and wherein the step of inspecting is performed with the light-transparent blank affixed to the shaping machine.

3. The method of claim 1, wherein the step of furnishing includes the step of
    affixing the light-transparent blank to a rotatable spindle of a shaping machine, and wherein the step of inspecting is performed with the light-transparent blank affixed to the rotatable spindle of the shaping machine.

4. The method of claim 1, including an additional step, after the step of inspecting, of
    correcting a shape of the trial parabolic surface responsive to the interference pattern to produce a final parabolic surface having a final parabolic focus coincident with the spherical-segment center.

5. The method of claim 4, wherein the step of furnishing includes the step of
    affixing the light-transparent blank to a shaping machine, and wherein the steps of inspecting and correcting are performed with the light-transparent blank affixed to the shaping machine.

6. The method of claim 1, wherein the step of forming the spherical-segment surface includes the step of
    applying a reflective coating to the spherical-segment surface.

7. The method of claim 1, wherein the step of forming the spherical-segment surface includes the step of
    forming a spherical-segment cavity.

8. The method of claim 1, wherein the step of forming the spherical-segment surface includes the step of
    forming a spherical-segment protrusion.

9. The method of claim 1, including an additional step, prior to the step of inspecting, of
    positioning a spherical retroreflector external to the first end of the light-transparent blank with a spherical-retroreflector center coincident with the spherical-segment center.

10. A method for fabricating and inspecting an optical element, comprising the steps of
    furnishing a light-transparent blank having a furnished lateral surface and an element axis; thereafter
    forming a spherical-segment surface in the light-transparent blank at a first end thereof, wherein the spherical-segment surface has a spherical-segment center on the element axis;
    forming a trial parabolic lateral surface in the furnished lateral surface of the light-transparent blank, wherein the trial parabolic lateral surface has a trial-surface parabolic focus coincident with the spherical-segment center; thereafter
    inspecting the trial parabolic lateral surface by
        directing a source light beam from a light source through the light-transparent blank parallel to the element axis and against the trial parabolic lateral surface, whereupon a reflected light beam reflects back substantially parallel to the source light beam but oppositely directed to the source light beam, and
        optically interfering the reflected light beam with the source light beam to produce an interference pattern; and thereafter correcting a shape of the trial parabolic surface responsive to the interference pattern to produce a finished lateral surface in the form of a final parabolic lateral surface having a final parabolic focus coincident with the spherical-segment center.

11. The method of claim 10, wherein the step of forming a spherical-segment surface includes the step of
    applying a reflective coating to the spherical-segment surface.

12. The method of claim 10, wherein the step of forming a spherical-segment surface includes the step of
    forming a spherical-segment cavity.

13. The method of claim 10, including an additional step, prior to the step of inspecting, of
    positioning a spherical retroreflector external to the light-transparent blank and along the element axis with a spherical retroreflector center coincident with the spherical-segment center.

14. The method of claim 10, wherein the step of forming the trial parabolic lateral surface includes the step of
    forming the trial parabolic surface by grinding.

15. The method of claim 10, wherein the step of correcting the shape of the trial parabolic surface includes the step of
    correcting the shape by polishing.

16. A method for fabricating and inspecting an optical element, comprising the steps of
    furnishing a light-transparent blank having an element axis;
    affixing the light-transparent blank to a shaping machine; thereafter
    forming a spherical-segment surface in the light-transparent blank at a first end thereof, wherein the spherical-segment surface has a spherical-segment center on the element axis;
    grinding and polishing a trial parabolic surface in a lateral surface of the light-transparent blank spaced apart from the element axis, wherein the trial parabolic lateral surface has a trial-surface parabolic focus coincident with the spherical-segment center; thereafter
    inspecting the trial parabolic surface by
        directing a source light beam from a light source through the light-transparent blank parallel to the element axis and against the trial parabolic surface, whereupon a reflected light beam reflects back substantially parallel to the source light beam but oppositely directed to the source light beam, and
        optically interfering the reflected light beam with the source light beam to produce an interference pattern; and thereafter
    correcting a shape of the trial parabolic surface responsive to the interference pattern using the shaping machine to produce a final parabolic surface, wherein the steps of inspecting and correcting are performed with the light-transparent blank affixed to the shaping machine.

17. The method of claim 16, wherein the step of forming the spherical-segment surface includes the step of
    applying a reflective coating to the spherical-segment surface.

18. The method of claim 16, wherein the step of forming the spherical-segment surface includes the step of
    forming a spherical-segment cavity.

19. The method of claim 16, wherein the step of forming the spherical-segment surface includes the step of
    forming a spherical-segment protrusion.

20. The method of claim 16, including an additional step, prior to the step of inspecting, of
    positioning a spherical retroreflector external to the light-transparent blank and along the element axis with a spherical retroreflector center coincident with the spherical-segment center.

* * * * *